United States Patent
Ilhan et al.

(10) Patent No.: US 6,218,138 B1
(45) Date of Patent: Apr. 17, 2001

(54) SYNTHESIS OF BETA-LACTAM ANTIBIOTICS WITH IMMOBILIZED PENICILLIN AMIDASE

(75) Inventors: Ferhat Ilhan, Atahesir; Dieter Kraemer, Mainz, both of (DE)

(73) Assignee: Unifar Kimya Sanayi ve Ticaret A.S., Istanbul (TM)

( * ) Notice: Subject to any disclaimer, the term of this patent is extended or adjusted under 35 U.S.C. 154(b) by 0 days.

(21) Appl. No.: 09/318,732

(22) Filed: May 26, 1999

(30) Foreign Application Priority Data

May 26, 1998 (DE) ............................................. 198 23 332

(51) Int. Cl.⁷ ............................ C12P 37/04; C12P 35/04; C12N 11/14; C12N 11/02; C12N 11/08
(52) U.S. Cl. ............................ 435/45; 435/43; 435/47; 435/50; 435/176; 435/177; 435/180
(58) Field of Search ................................. 435/43, 44, 45, 435/47, 48, 49, 50, 176, 177, 178, 180

(56) References Cited

U.S. PATENT DOCUMENTS

| | | | |
|---|---|---|---|
| 4,250,260 | * | 2/1981 | Ruhrbach et al. .................. 435/176 |
| 5,326,698 | * | 7/1994 | Kasche et al. ...................... 435/231 |
| 5,470,717 | * | 11/1995 | Clausen et al. ...................... 435/47 |
| 6,048,708 | * | 4/2000 | Clausen et al. ...................... 435/45 |

FOREIGN PATENT DOCUMENTS

9417800 * 8/1994 (WO).
9623897 * 8/1996 (WO).

* cited by examiner

*Primary Examiner*—David M. Naff
(74) *Attorney, Agent, or Firm*—Oblon, Spivak, McClelland, Maier & Neustadt, P.C.

(57) ABSTRACT

Beta-lactam antibiotics are synthesized by reacting an amino-beta-lactam component with a corresponding amino-group-containing acylating side-chain component in the presence of penicillin amidase from *E. coli* covalently immobilized on support particles. The resulting beta-lactam antibiotic product is solubilized by adding an acid such as sulfuric acid to lower the pH to 1.0 at a temperature in the range of 0° C. to +5° C. The immobilized penicillin amidase is substantially inactivated by the acid. After separating the beta-lactam antibiotic product, the immobilized penicillin amidase is substantially reactivated for reuse in antibiotic synthesis by treatment with a buffer having about a neutral pH. Antibiotics that can be produced include ampicillin, amoxicillin, cephalexin, cefaclor and cefadroxil. Support particles that can be used include particles having a macroporous structure and a particle diameter of 10–1000 µm, particles having oxirane groups, particles made of a synthetic polymer and inorganic particles such as porous glass particles.

17 Claims, No Drawings

SYNTHESIS OF BETA-LACTAM ANTIBIOTICS WITH IMMOBILIZED PENICILLIN AMIDASE

BACKGROUND OF THE INVENTION

1. Field of the Invention

The present invention relates to a method of synthesis of β-lactam antibiotics.

2. Discussion of the Background

It has long been known that beta-lactam antibiotics can be formed from their respective nucleus and side-chain components via enzymatic pathways (C. A. Claridge et al., Nature, Vol. 187;237, 1960).

From more recent studies it is known that a beta-lactam antibiotic, for example amoxicillin, synthesized via enzymatic pathways, has higher purity and accordingly lower toxicity than amoxicillin synthesized by chemical pathways (PCT WO 94/17800).

The general interest for industrially practical processes for enzymatically synthesizing beta-lactam antibiotics is correspondingly great.

In order to achieve this objective, a series of technical problems must be overcome or needs fulfilled, especially:

a) The need to maximize the desired synthesis reaction catalyzed by the enzyme and to minimize the undesired side reactions catalyzed by the same enzyme, such as hydrolysis of the activated side-chain components and of the beta-lactam antibiotic (see the reaction mechanism below).

Reaction mechanism

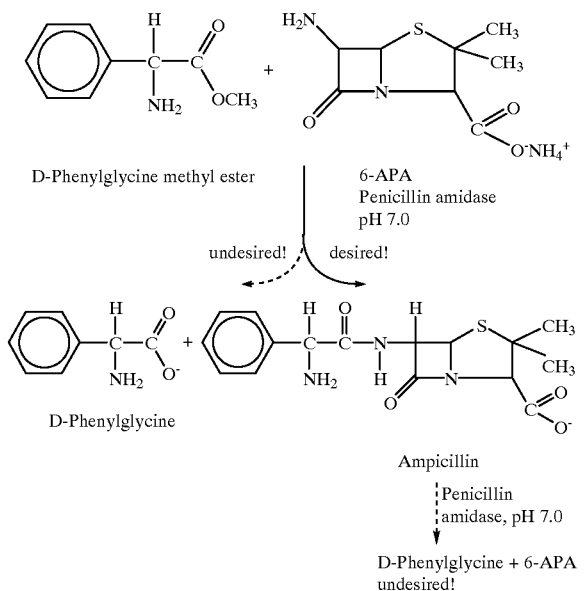

b) The need to isolate the product in a way which permits reuse of the biocatalyst, or, in other words, the enzyme.

Even now are numerous patent applications which have already been published, as well as patents granted, which claim decisive advances in solving these problems and which are based on experimental findings obtained with enzymes immobilized on insoluble carrier particles, usually covalently; in other words with systems, developed in the most recent decades, for reuse of enzymes.

It is, therefore, self-evident that the operational stability (O-ST) of these immobilized enzymes must be studied under practical conditions, in order to obtain an appraisal of the industrial productivity of such a biocatalyst.

In most cases, however, investigators have been satisfied with a minimum of tests, namely with testing of a single batch.

The result obtained in this way was then often generalized in a global claim, without regard to a fact well-known to the experts, that a result obtained from only a single batch is usually misleading for characterization of an immobilized enzyme and a reaction catalyzed thereby, specifically for the following reasons:

1. The activity measured for the first use of a covalently immobilized enzyme is usually much too high, because free enzyme is often still present. This free enzyme is adsorbed non-covalently on the support material, thus giving a false impression of higher activity of the "immobilized" enzyme, specifically until it has been eliminated by interaction with the substrate and by washing processes, such elimination lasting at least one cycle of use and usually several cycles.

In this connection, it must be recalled that immobilized enzymes are employed mainly because of their ready reusability, or in other words, their usability over many batch cycles, and because of the purity of the products which have been synthesized under these conditions.

The purity laws automatically preclude contamination by free enzyme; therefore, the product from the first batch should not be used in any case for the synthesis of pharmaceuticals.

2. Substrate and product molecules can be adsorbed on the support material on which the enzyme is covalently immobilized, and thus can elude analytical determination thereby falsifying the balance between synthesis and hydrolysis reactions.

This phenomenon is relevant in particular for the first batch. Thereafter a kind of stable state is established by saturation of the adsorbing support surface. In this context, analytical methods which consider only the dissolved constituents are misleading. In order to achieve a correct balance, only methods which permit solubilization of all molecules present should be used.

3. The immobilized enzyme almost always loses activity in the course of its use, but especially during the first three cycles of use.

For all of these reasons it is advisable to run at least four successive batch cycles in order to obtain a somewhat correct estimate of product yield, degree of conversion of the reaction and O-ST of the biocatalyst.

The test methods must obviously be significant, meaning that the product must be isolated if possible and its composition must be studied by, for example, HPLC or NM R. Samples taken from the heterogeneous product or reaction mixture must be solubilized before they are tested.

These rules have not been followed, however, in most of the patent applications and granted patents. To the knowledge of the present inventors, there is currently only a single application (PCT WO 96/23897, Chemferm, Boesten ct al.) which provides data on the O-ST of the biocatalyst obtained by testing of five successive batch cycles, with a degree of conversion of about 40% of the nucleus components.

Another critical aspect in the field of enzymatic synthesis of beta-lactam antibiotics relates to isolation of the product. Isolation of the product is problematic for the following reasons:

The antibiotic synthesized in this way is normally obtained as a heterogeneous mixture of solid and dissolved product, which must be separated from the biocatalyst, or in other words, the immobilized enzyme, which is also solid. In this regard, Clausen et al. (PCT WO 96/02663 A1) have published a process for synthesis of beta-lactam antibiotics at constantly high concentration of the reactants, wherein the desired product is obtained mainly as a solid product in the form of small crystals, which are continuously separated from the reactor by passing them through a sieve, which holds up the biocatalyst, into a centrifuge, in which such crystals are isolated. The centrifuge supernatant is pumped back into the reactor via a tank, in which further substrate is added. This process offers a noteworthy advance, in that the product is removed rapidly from the reaction medium via crystallization and centrifugation, and consequently cannot be hydrolyzed to undesired secondary products.

Despite this advantage, the process does not permit problem-free continuous operation in the stirred reactor.

The risk exists that in this process, which in principle is a wet-sieve process, the bottom sieve of the reactor will gradually become fouled because of the non-uniformity of grain sizes, and that the accumulation of solid products will form in the reactor itself a pasty mass at first and ultimately a solid conglomerate of product and catalyst particles, thus making further operation of the reactor impossible.

In summary, it can be said that the prior art known prior to this invention leaves unsolved the true problem, namely the clean separation of the product in combination with reusability, meaning reusability of the biocatalyst. A need, therefore, continues to exist for such a process which can be achieved without problems in the stirred reactor or-in the fixed-bed reactor.

SUMMARY OF THE INVENTION

Accordingly, one object of the present invention is to provide a process of enzymatic synthesis of β-lactam antibiotics which achieves the clean separation of enzyme biocatalyst from the product and the reusability of the biocatalyst, especially in a stirred reactor or a fixed-bed reactor.

Briefly, this object and other objects of the present invention as hereinafter will become more readily apparent can be attained in a process of synthesizing an amino-group-containing beta-lactam antibiotic, comprising: reacting an amino-beta-lactam component and the corresponding amino-group-containing acylating side-chain component in the presence of a biocatalyst of the immobilized enzyme penicillin amidase from $E.$ $coli$ covalently immobilized on support particles, thereby forming a β-lactam antibiotic product; adding an acid to the obtained suspension of product and immobilized enzyme to pH 1.0 over the temperature range of 0° C., to +5° C., thereby solubilizing the product; separating the product from the immobilized enzyme; and then regenerating the enzyme biocatalyst in terms of its activity by treatment with a buffer in the neutral pH range at a temperature of about +5° C.

DETAILED DESCRIPTION OF THE PREFERRED EMBODIMENTS

The example of the beta-lactam antibiotic ampicillin has shown that the problem of clean separation of enzymatically synthesized ampicillin and the immobilized enzyme used for the purpose can be solved by adding a strong acid to the suspension of product and immobilized enzyme at a temperature of 0° C. to +2° C. until a pH of 1.0 is reached. At this pH all reaction products dissolve rapidly. The products solubilized in this manner can be easily separated, via the bottom sieve of the reactor in the case of a stirred reactor and by elution in the case of a fixed bed reactor, while the immobilized enzyme remains in the respective reactor. The immobilized enzyme is inactivated almost completely, i.e., to an extent greater than 90%, by the acid treatment.

It has now also been found that the enzyme inactivated in this manner can be reactivated almost completely, i.e., to an extent greater than 90%, by adding a buffer of neutral pH to the inactivated immobilized enzyme (I-E) and keeping the I-E in suspension in this buffer for several hours at a temperature of about +5° C.

This regenerability of the I-E after total loss of its activity is the feature of this invention that is not expected by the person skilled in the art. The regenerability according to the invention of the I-E is fully preserved even after several batches and the associated several acid treatments.

This method functions with the penicillin amidase enzyme from $E.$ $coli$ (E.C. 3.5.1.11.) covalently immobilized on macroporous beads of polymethacrylate components. It is likely that this method will also function with penicillin amidases from other microorganisms such as $Bacillus$ $megatherium$ or $Xanthomonas$ $Citrii$.

The method should function with any beta-lactam antibiotic (BLA) which has a free amino group in the side chain, for example with amoxicillin, cephalexin, cephadroxil, cefaclor or cefroxadine.

The immobilized enzyme (I-E)

The penicillin amidase enzyme from $E.$ $coli$ (E. C. 3.5.1.11) covalently bound to Eupergit C® is employed for enzymatic synthesis of the beta-lactam antibiotic ampicillin. Such a biocatalyst is synthesized by the FZB Co. (Berlin), for example, and sold under the name PharmaKAT-PcA. This enzyme was used primarily to prepare the products in the experiments leading to the invention.

The support material

Eupergit C® is a bead-like support material for covalent immobilization of enzymes. It is made and marketed by Röhm GmbH (D-64293 Darmstadt). The particle diameter of Eupergit C® is 50–250 microns. It is a copolymer of methacrylamide, N,N'-methylenebismethacrylamide, glycidyl methacrylate and allyl glycidyl ether. Enzymes can be bound covalently to Eupergit C® by means of covalent bonds formed therebetween, for example, the amino groups of the enzyme and the oxirane groups of the glycidyl components of Eupergit C®. This bonding is stable to acids, and so the acid treatment of the invention does not cause detachment of the enzyme from the immobilizate. Eupergit C® itself has adequate acid stability, meaning that it is dimensionally stable and retains its bed volume even after prolonged action of acid, in other words neither swelling nor shrinkage of the immobilizate is observed during pH changes from pH 7.5 to pH 1.0 and vice versa. This is very important in particular for the application of the invention in the fixed-bed reactor. Any other support material which meets the above criteria would also be suitable instead of Eupergit C® for the process of the invention, an example being particles of porous glass, appropriately derivatized with groups which are acid stable and permit formation of acid-stable covalent bonds to the enzyme molecule.

Loss of activity of I-E in the acid pH range

Penicillin amidase covalently bound to Eupergit C® was synthesized and sold under the trade name Eupergit-PcA years ago by Röhm Pharma, a company that no longer exists. An applications-related pamphlet describing the use of this biocatalyst for synthesis of 6-aminopenicillanic acid mentions the loss of activity of the immobilized enzyme in the acid pH range and recommends precautions to minimize this risk.

As expected, almost complete loss of activity (>95%) was observed when we added cold 12.5–25% sulfuric acid to a cooled aqueous suspension of PharmaKAT-PcA and the product mixture of enzymatic ampicillin synthesis, in order to dissolve the undissolved ampicillin at pH 1.0 so that it could be removed by filtration from the biocatalyst particles. This type of solubilization and separation of the ampicillin from the product mixture proved to be an efficient and easily performed method, but, as expected, at the cost of almost complete loss of activity of the biocatalyst.

The solubilization of amino-group-containing beta-lactam antibiotics from their product mixture by acidification after separation from the biocatalyst (or in other words in the absence thereof!) is disclosed in U.S. Pat. No. 5,470,717.

Regeneration of the activity of the enzyme inactivated by acid

It has been surprisingly found that the biocatalyst inactivated as described above can be successfully regenerated almost completely, meaning that its original enzyme activity is successfully regained, by incubating the biocatalyst in 0.1 molar potassium phosphate buffer at pH 7.5 for a period of 8–30 hours at about +5° C.

Using the same immobilized enzyme sample in all cases, the enzymatic procedure was performed four times in succession, in other words over four consecutive synthesis cycles, without noticeable loss of enzyme activity, enzyme activity being defined as the quantity of synthesized product per unit of synthesis time per unit of enzyme quantity used. After each synthesis step the pH of the product suspension was adjusted to 1.0 at 0° C. with sulfuric acid; the product solution was then filtered off; the I-E remaining on the filter in the reactor was first washed with water and then buffer was added to the I-E obtained. The mixture was incubated for 16 hours at pH 7.5 and about +5° C. Further experimental details and results are provided in the Examples.

The applicability of the process of the invention for enzymatic BLA synthesis in the stirred reactor and in the fixed-bed reactor is demonstrated in the Examples. From the results it can be concluded that the operational stability (O-ST) of the I-E is more than four synthesis cycles provided the procedure of the present invention is followed.

Regenerability of I-E after inactivation by acid: an INNOVATION compared with the prior art The ability of the immobilized enzyme (I-E) to regenerate after its almost complete inactivation by acid could not have been suggested by the prior art. It has been known that, after inactivation at pH 2.0, the free enzyme can be regenerated to about 40% of its original activity by incubation in neutral buffer, whereas the reactivability of the enzyme immobilized on Eupergit C® instead "diminished" (U. Haufler, Dissertation, page 103, Bremen University, 1987 as well as Haufler et al., DECHEMA Biotechnol. Conf(1988), Volume Date 1987, 1., 345–350). However, such a reduction in regenerability was not confirmed in the studies of the invention. To the contrary, even after four consecutive inactivations under acid stress, or in other words at a hydronium ion concentration which was ten times higher than in the experiments of U. Haufler and which, moreover, was repeated four times, the I-E treated in the manner of the invention was reactivated to almost 100% (>95%) of its original activity and O-ST relative to enzymatic ampicillin synthesis.

Reactors for performing the process of the invention

As already mentioned, the process of the invention can be performed in any type of reactor which is suitable for the use of immobilized enzymes for biocatalytic purposes.

If a stirred-tank reactor is employed, it must be equipped with a bottom sieve or with filter candles in order to hold up the biocatalyst, or in other words the I-E, in the reactor, specifically during all individual steps of the procedure, i. e., during enzymatic synthesis as well as during solubilization of the product by acid addition, during separation of the product by filtration, during regeneration of the immobilized enzyme by incubation in buffer, and during recharging of the reactor with substrate solution for the next cycle.

All of these steps can be performed conveniently in the same reactor, in a one-pot process as it were.

Suitable as fixed-bed reactors (FBR) are columns for preparative chromatography (on the production scale), as sold by several companies (for example, Merck/Darmstadt), provided they are made of acid-stable materials and are equipped with acid-stable supply and discharge tubes whose inside diameter is large enough to permit relatively high flowrates. The columns must also be equipped with a temperature-control jacket through which cooling fluid can be passed. In addition, the standard systems must be supplemented with devices which permit acid or buffer to be recirculated through the column and to be cooled efficiently by additional external cooling systems. Furthermore, suitable pumps, as well as measuring instruments for pressure, temperature and flowrate, are needed for operation and control of the FBR. Systems which permit automatic control are desirable.

An FBR is operated as follows:

The substrate solution is pumped continuously at constant flowrate through the FBR column (containing I-E) and the product formed therein is collected at the outlet of the column in a tank for further purification. As soon as the flowrate decreases or the pressure in the column rises, which is an indication that the column is becoming gradually fouled by product crystals, the substrate feed is stopped and a supply of acid which has been cooled to 0° C. by passage through a cooling batch is started. This acid stream is recirculated continuously through the column, which is also being cooled by means of its temperature-control jacket, until all solid product has dissolved in the acid, which is recognized by the fact, for example, that the same flowrate as at the start of substrate addition has been reached. At this point in time the acid recirculation is stopped, and the acid is collected in a separate tank while cold washing water is supplied at the same time.

The washing water is recirculated through the column for about 20 minutes, Then the recirculation of water is stopped. The water is collected in a tank, while at the same time the supply of cold regeneration buffer is started. This buffer is recirculated through the column for 12–16 hours at +5° C. Then the buffer recirculation is stopped. The buffer is collected in a tank, while at the same time the supply of substrate solution is started, after the column temperature has been adjusted to +25° C.

The result of four consecutive sequences of operation of such a column on the laboratory scale is presented in Examples 7–10. The results show that an FBR permits better control of the reaction with regard to synthesis than is possible in the stirred tank. However, an FBR involves considerably greater engineering complexity and the greater risks of faulty control that are inevitably associated therewith.

Summation

The results of the experiments in the FBR and in the stirred tank show the technical applicability of the inventive principle of product isolation in the presence of the biocatalyst at pH 1.0 and the regeneration of the biocatalyst by incubation in neutral buffer. In the present scope of application, namely the enzymatic synthesis of beta-lactam antibiotics, it was not practical to examine whether this principle also functions in the alkaline pH range.

Abbreviations used in the text:

| I-E: | immobilized enzyme | FBR: | fixed-bed reactor |
|---|---|---|---|
| O-ST: | operational stability of the activity of an I-E | SLR: | stirred tank reactor |
| | | HPLC: | high performance liquid chromatography |
| DEI-water: | deionized water | | |
| g: | gram | NMR: | nuclear magnetic resonance |
| ml: | milliliter | | |
| 6-APA: | 6-aminopenicillanic acid | pH: | negative logarithm (to the base 10) of the molar hydrogen ion concentration |
| 7-ADCA: | 7-aminodesacetoxy-cephalosporanic acid | | |
| PcA: | penicillin amidase | PHE-GLY: | D-phenylglycine |
| E. coli: | Escherichia Coli | PHE-GLY-ME: | D-phenylglycine methyl ester |

Having now generally described the invention, a further understanding can be obtained by reference to certain specific Examples which are provided herein for purpose of illustration only and are not intended to be limiting unless otherwise specified.

EXAMPLES

Example 1
Preparation of the Substrate Solution for Experiments in the Stirred Tank Reactor (SLR)

To 20 ml of deionized water there were added 4.3 g of 6-aminopenicillanic acid (6-APA) and 10 g of phenylglycine methyl ester hydrochloride. Approximately 38 ml of ammonia (1.25 molar aqueous solution) was added dropwise with stirring and cooling to 18–22° C., such that the pH of the mixture did not exceed a value of pH 8.0 at the start and a pH of 7.0 at the end of the dissolution process. In this way, about 65 ml of substrate solution was obtained. The solution was weighed and, after removal of a small quantity (about 1 g) for analytical purposes, was used quantitatively for one enzymatic synthesis in the stirred reactor.

Example 2
Enzymatic Synthesis in the Stirred Tank Reactor STR/First Batch

The substrate solution of Example 1 was added with stirring to 20 grams (moist weight) of penicillin amidase immobilized on Eupergit C®. PharmaKAT-PcA, a commercial product of FZB Biotechnik GmbH of Berlin, was used for this purpose.

The suspension was stirred for 180 minutes at 23–25° C., while the pH was maintained constant at pH 7.0 by addition of small quantities of 1.25 molar ammonia.

The mixture was then cooled to 0° C. and thereafter 2.5 molar (approximately 25%) sulfuric acid was added dropwise with stirring, constant cooling to 0° C. and precise pH control until a constant pH of 1.0 was achieved. Then this solution was stirred for a further 10–20 minutes with cooling to 0° C. and thereafter was removed by suction through the bottom sieve of the reactor. A 1.0 g amount of the filtrate was diverted for analytical determinations. The main quantity was used for isolation of the reaction products. For this purpose the pH was adjusted to pH 5.1 by addition of concentrated ammonia, while the temperature of the mixture was kept consistently at 0° C. by cooling. The mixture was stirred for 2 hours at 0° C. and pH 5.1. Meanwhile a crystalline product was precipitated. It was removed by filtration and washed with cold water, rapidly suctioned and dried overnight in vacuum at +30° C. A 7.67 g amount was obtained. This product was subjected to HPLC to determine its content of ampicillin trihydrate; result: 51% ampicillin trihydrate, corresponding to 3.9 g (9.67 mmol), which corresponds to a yield of 48% relative to the feed quantity of 6-APA.

The immobilized enzyme remaining on the filter in the STR was suspended in 100 ml of cold DEI-water and adjusted to a pH of 6.5–7.0 with cold 1.25 molar ammonia with stirring and cooling, further stirred for 10 minutes and suctioned. Then 100 ml of cold K phosphate buffer (0.1 molar, pH 7.5) was added. The mixture was stirred gently for 3 hours at +5° C. and then left in the reactor without further stirring for 12 hours at +5° C.

Example 3
Enzyme Synthesis in the STR/Second Batch

The phosphate buffer from Example 2 was removed by suction from the I-E, thus leaving the I-E on the bottom strainer in the reactor. There it was washed with 50 ml of 23° C. water and suctioned. Then substrate was added to the I-E as in Example 1.

The suspension of I-E in the substrate solution was stirred for 180 minutes at 23–24° C. In this step and in the subsequent further process, exactly the same procedure as described for Example 2 was followed.

Result: 7.46 g of crystalline product.

Content of ampicillin trihydrate: 3.4 g, corresponding to 42% yield relative to 6-APA.

Example 4
Enzyme Synthesis in the STR/Third Batch

The phosphate buffer from Example 3 was removed by suction from the I-E, and then exactly the same procedure as described for Example 2 was followed.

Result: 7.3 g of crystalline product.

Content of ampicillin trihydrate: 4.0 g, corresponding to 50% yield relative to 6-APA.

Example 5
Enzyme Synthesis in the STR/Fourth Batch

The phosphate buffer from Example 4 was removed by suction from the I-E, and then exactly the same procedure as described for Example 2 was followed.

Result: 7.32 g of crystalline product.

Content of ampicillin trihydrate: 3.2 g, corresponding to 40% yield relative to 6-APA.

As a relative measure for the ratio of synthesis to hydrolysis, the ratio of areas of ampicillin trihydrate to D-phenylglycine in the HPLC diagram was 1.1.

Example 6
Preparation of the Substrate Solution for Experiments in the Fixed-Bed Reactor (FBR)

A 16.1 g amount of 6-APA and 15.0 g of D-phenylglycine methyl ester hydrochloride were dissolved in 190 ml of DEI-water with stirring at 24–25° C. by careful addition of ammonia (2.4 molar) and adjusted to a pH of 7.0. About 45 ml of ammonia in total was added for this purpose.

Example 7
Enzymatic Synthesis in the Fixed-Bed Reactor (FBR)/First Use

An FBR was filled to a bed volume of 110 ml with an aqueous suspension of Penicillin amidase immobilized on Eupergit C® (PharmaKAT-PcA) in DEI-water. The reactor was made of stainless steel. Its diameter was 43 millimeter (mm) and its height was 150 mm. The filled height of the fixed bed was 76 mm.

Substrate solution (according to Example 6) was introduced from above onto this fixed bed, passed through the fixed bed at a flowrate of 2.5 ml per minute and collected in fractions. The contents of ampicillin, 6-APA, D-phenylglycine methyl ester and D-phenylglycine in individual fractions were determined with HPLC. (See the table for individual results.) As a relative measure of synthesis/hydrolysis, the ratio of areas of ampicillin to D-phenylglycine in the HPLC diagram was 0.83.

After 150 ml of reacted substrate solution had been collected, the supply of substrate solution was stopped and 1.25 molar sulfuric acid was passed through the fixed bed at a temperature of 0° C. until a pH of 1.0 was reached at the outlet of the fixed-bed reactor. As soon as the pH measurement at the fixed-bed outlet showed a pH of 1.0 for a period of 30 minutes, the supply of sulfuric acid was stopped. Following a washing step with cold water, the supply of potassium phosphate buffer (0.1 molar, pH 7-5) at a temperature of +5° C. was started. As soon as a pH of 7.5 was reached at the outlet of the reactor, the buffer stream through the column was switched to recirculation, or in other words to flow in a closed loop, which was maintained for 12 hours at a flowrate of 1 ml/min and a temperature of +5° C.

In this manner the biocatalyst was regenerated for the next use for synthesis of ampicillin.

Example 8
Enzymatic Synthesis in the Fixed-Bed-Reactor (FBR)/Second Use

The immobilized enzyme regenerated by incubation with buffer from Example 7 was washed with DEI-water in the FBR. Substrate solution (according to Example 6) was introduced from above onto this fixed bed, passed through the fixed bed at a flowrate of 1.7 ml per minute and collected in fractions at the reactor outlet. The contents of ampicillin, 6-APA, D-phenylglycine methyl ester and D-phenylglycine in individual fractions were determined with HPLC.

Individual results: see table.

Relative measure of synthesis to hydrolysis (corresponding to ratio of areas in the HPLC diagram) was 1.9.

After 150 ml of reacted substrate solution had been collected, the supply of substrate solution was stopped. The further procedure was identical to that of Example 7.

Example 9
Enzymatic Synthesis in the Fixed-Bed Reactor (FBR)/Third Use

The regenerated immobilized enzyme from Example 8 was used, and otherwise the same procedure as described for Example 8 was followed, with the difference that the flowrate was 1 ml per minute and the substrate supply was stopped after collection of 170 ml.

Individual results: see table.

Relative measure of synthesis to hydrolysis (corresponding to ratio of areas in the HPLC diagram) was 2.2.

Example 10
Enzymatic Synthesis in the Fixed-Bed Reactor (FBR)/Fourth Use

The regenerated immobilized enzyme from Example 9 was used, and otherwise the same procedure as described for Example 9 was followed, with the difference that the substrate supply was stopped after collection of 304 ml.

Individual results: see table.

Relative measure of synthesis to hydrolysis (corresponding to ratio of areas in the HPLC diagram): 2.1.

Example 11
Performance of the HPLC Studies: Method and Material

A Hewlett-Packard HP 1100 instrument was used for the HPLC studies.

Sample preparation

A 1 g amount of solution (in the stirred-reactor experiments after solubilization by $H_2SO_4$; in the FBR experiments directly from the Column eluate) was diluted with phosphate buffer (25 millimolar; pH 6.5) to a final volume of 25 ml.

For testing of solid samples, 50 mg of product was dissolved in 50 ml of phosphate buffer (25 millimolar, pH 6.5).

Formulation of the standard solutions

A 50 mg amount of ampicillin trihydrate or 50 mg of D-phenylglycine or 50 mg of 6-APA or 50 mg of D-phenylglycine methyl ester hydrochloride respectively was dissolved in each case in 50 ml of phosphate buffer (25 millimolar, pH 6.5).

Method: gradient method

Eluent A: 25 millimolar phosphate buffer (pH 6.5)

Eluent B: acetonitrile

Flowrate: 1 ml/min

Wavelength: 215 nm

Injection volume. 20 microliter

Analysis duration: 20 minutes

HPLC column: MAXIL 5C18 (250×4.60 mm), 5 micron

Table of results of enzymatic ampicillin synthesis in the FBR (corresponding to Examples 7 to 10)

| Guide value for elution volume * | Components in the product mixture | First use Flowrate 2.5 ml/min HPLC area/elution vol. | | Second use Flowrate 1.7 ml/min HPLC area/elution vol. | | Third use Flowrate 1.0 ml/min HPLC area/elution vol. | | Fourth use Flowrate 1.0 ml/min HPLC area/elution vol. | |
|---|---|---|---|---|---|---|---|---|---|
| 100 ml | PHE-GLY | 10242 | } 100 ml | 9399 | } 120 ml | 8094 | } 100 ml | (n.t.) | |
|  | 6-APA | 49892 |  | 44959 |  | 39514 |  |  |  |
|  | AMPICILLIN | 9725 |  | 16293 |  | 10187 |  |  |  |
|  | PHE-GLY-ME | 56103 |  | 26339 |  | (n.t.) |  |  |  |
| 150 ml | PHE-GLY | 12468 | } 150 ml | 11266 | } 150 ml | 17606 | } 150 ml | 17501 | } 160 ml |
|  | 6-APA | 50789 |  | 42381 |  | 40866 |  | 24240 |  |
|  | AMPICILLIN | 10308 |  | 21602 |  | 37134 |  | 34237 |  |

-continued

Table of results of enzymatic ampicillin synthesis in the FBR (corresponding to Examples 7 to 10)

| Guide value for elution volume * | Components in the product mixture | First use Flowrate 2.5 ml/min HPLC area/elution vol. | Second use Flowrate 1.7 ml/min HPLC area/elution vol. | Third use Flowrate 1.0 ml/min HPLC area/elution vol. | Fourth use Flowrate 1.0 ml/min HPLC area/elution vol. | |
|---|---|---|---|---|---|---|
|  | PRE-GLY-ME | 66289 | 54714 | 36732 | 2193** |  |
| 200 ml | PHE-GLY | not tested | (n.t.) | (n.t.) | 18407 | ⎫ |
|  | 6-APA | (n.t.) |  |  | 23848 | ⎬ 200 ml |
|  | AMPICILLIN |  |  |  | 37184 | ⎭ |
|  | PHE-GLY-ME |  |  |  | 10947** |  |
| 250 ml | PHE-GLY | (n.t.) | (n.t.) | (n.t.) | 18901 | ⎫ |
|  | 6-APA |  |  |  | 24491 | ⎬ 260 ml |
|  | AMPICILLIN |  |  |  | 39567 | ⎭ |
|  | PHE-GLY-ME |  |  |  | 15016 |  |
| 300 ml | PHE-GLY | (n.t.) | (n.t.) | (n.t.) | 17882 | ⎫ |
|  | 6-APA |  |  |  | 23806 | ⎬ 300 ml |
|  | AMPICILLIN |  |  |  | 37308 | ⎭ |
|  | PHE-GLY-ME |  |  |  | 17246 |  |

Abbreviations:
PHE-GLY → D-phenylglycine
6-APA → 6-aminopenicillanic acid
AMPICILLIN → ampicillin trihydrate
PHE-GLY-ME → D-phenylglycine methyl ester
*The exact value of the elution volume is listed in the respective column
**Retardation of the ester for an unknown reason The disclosure of German priority Application No. 198 23 332.9-42 filed May 26, 1998 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A process of synthesizing an amino-group-containing beta-lactam antibiotic, comprising:

reacting an amino-beta-lactam component and a corresponding amino-group-containing acylating side-chain component in the presence of a biocatalyst comprising penicillin amidase from *E. coli* covalently immobilized on support particles to form a reaction product mixture comprising a β-lactam antibiotic product; solubilizing the beta-lactam antibiotic product by adding an acid to the beta-lactam antibiotic product to lower the pH to 1.0 at a temperature in the range of 0° C. to +5° C., said acid substantially inactivating said immobilized penicillin amidase;

separating the beta-lactam antibiotic product from the immobilized penicillin amidase and then substantially reactivating said immobilized penicillin amidase by treatment with a buffer having about a neutral pH to provide said immobilized penicillin amidase with an activity suitable for reuse in said process for synthesizing an amino-group-containing beta-lactam antibiotic.

2. The process according to claim 1, wherein reactivating said immobilized penicillin amidase is performed at a termperature of about +5° C.

3. The process according to claim 1, wherein the antibiotic synthesized is ampicillin, the amino-beta lactam component is 6-aminopenicillanic acid and the acylating side-chain component is D-phenylglycine methyl ester or D-phenylglycinamide.

4. The process according to claim 1, wherein the beta-lactam antibiotic synthesized is cephalexin, the amino-beta-lactam component is 7-aminodesacetoxycephalosporanic acid (7-ADCA) and the acylating side-chain component is D-phenylglycine methyl ester or D-phenylglycinamide.

5. The process according to claim 1, wherein the beta-lactam antibiotic synthesized is cefaclor, the amino-beta-lactam component is 3-chloro-7-aminodesacetoxycephalosporanic acid and the acylating side-chain component is D-phenylglycine methyl ester or D-phenylglycinamide.

6. The process according to claim 1, wherein the beta-lactam antibiotic synthesized is amoxicillin, the amino-beta-lactam component is 6-aminopenicillanic acid and the acylating side-chain component is D-p-hydroxyphenylglycine methyl ester or D-p-hydroxyphenylglycinamide.

7. The process according to claim 1, wherein the beta-lactam antibiotic synthesized is cefadroxil, the amino-beta-lactam component is 7-aminodesacetoxycephalosporanic acid (7-ADCA) and the acylating side-chain component is D-p-hydroxyphenylglycine methyl ester or D-p-hydroxyphenylglycinamide.

8. The process according to claim 1, wherein the support particles have a macroporous structure and a particle diameter of 10–1000 $\mu$m.

9. The process according to claim 8, wherein the support particles have oxirane groups for covalent immobilization of the penicillin amidase.

10. The process according to claim 9, wherein the oxirane-group-containing macroporous support particles comprise synthetic polymers.

11. The process according to claim 9, wherein the oxirane-group-containing macroporous support particles comprise inorganic material.

12. The process according to claim 11, wherein the inorganic support particles comprise porous glass.

13. The process according to claim 1, wherein all steps of said process are conducted in a stirred reactor, which is equipped with a bottom strainer.

14. The process according to claim 1, wherein all steps of said process are conducted in a fixed-bed reactor.

15. The process according to claim 1, wherein, for solubilization of the β-lactam antibiotic product a quantity of five per cent to fifty per cent sulfuric acid is added to cooled reaction product mixture until a pH of 1.0 is reached.

16. The process according to claim 1, wherein the buffer used for reactivating said immobilized penicillin amidase is a phosphate buffer with a molarity of 0.1–1.0 and a pH of 6.5–8.0.

17. The process according to claim 1, wherein the antibiotic product is ampicillin, amoxicillin, cephalexin, cefaclor or cefadroxil.

* * * * *

UNITED STATES PATENT AND TRADEMARK OFFICE
CERTIFICATE OF CORRECTION

PATENT NO. : 6,218,138 B1
DATED : April 17, 2001
INVENTOR(S) : Ferhat Ilhan and Dieter Kraemer It is certified that error appears in the above-identified patent and that said Letters Patent is hereby corrected as shown below:

Title page,
Delete Item [75] in its entirety and replace with -- Inventors: Ferhat Ilhan, Atahesir, of Turkey; Dieter Kraemer, Mainz, of DE --.

Column 2,
Line 51, "NM R" should read -- NMR --.

Column 3,
Line 40, "the present invention as hereinafter will become more readily apparent can be" should read -- the present invention, as hereinafter will become more readily apparent, can be --.

Column 4,
Line 25, "The immobilized enzyme (I-E)", should read -- The immobilized enzyme (I-E) --.
Lines 34-35, "R öhm GmbH" should read -- Röhm GmbH --.
Line 59, "Loss of activity of I-E in the acid pH range", should read -- Loss of activity of I-E in the acid pH range --.

Column 5,
Line 16, "Regeneration of the activity of the enzyme inactivated by acid", should read -- Regeneration of the activity of the enzyme inactivated by acid --.
Lines 43-44, "Regenerability of I-E after inactivation by acid: an INNOVATION compared with the prior art", should read -- Regenerability of I-E after inactivation by acid: an INNOVATION compared with the prior art --.
Line 64, "Reactors for performing the process of the invention" should read -- Reactors for performing the process of the invention --.

Column 6,
Line 64, "Summation" should read -- Summation --.

Column 7,
Line 11, "SLR" should read -- STR --.
Line 34, "SLR" should read -- STR --.

Column 10,
Line 50, "Injection volume" should read -- Injection volume: --.

UNITED STATES PATENT AND TRADEMARK OFFICE
CERTIFICATE OF CORRECTION

PATENT NO. : 6,218,138 B1
DATED : April 17, 2001
INVENTOR(S) : Ferhat Ilhan and Dieter Kraemer It is certified that error appears in the above-identified patent and that said Letters Patent is hereby corrected as shown below:

Column 11,
Table of Results, second column of table, line 1, "PRE-GLY-ME", should read
-- PHE-GLY-ME --.
Lines 58-59, "ter-mperature" should read -- tem-perature --.

Column 12,
Line 61, "strainer" should read -- sieve --.

Signed and Sealed this

Second Day of April, 2002

Attest:

Attesting Officer

JAMES E. ROGAN
*Director of the United States Patent and Trademark Office*